United States Patent
Melnichuk et al.

(12)

(10) Patent No.: US 6,919,488 B2
(45) Date of Patent: Jul. 19, 2005

(54) PROCESS FOR PRODUCING SALEABLE LIQUIDS FROM ORGANIC MATERIAL

(75) Inventors: Larry Jack Melnichuk, Burlington (CA); Karen Venita (Sue) Kelly, Burlington (CA)

(73) Assignee: Woodland Chemical Systems, Inc., Mississauga (CA)

( * ) Notice: Subject to any disclaimer, the term of this patent is extended or adjusted under 35 U.S.C. 154(b) by 237 days.

(21) Appl. No.: 10/441,273

(22) Filed: May 20, 2003

(65) Prior Publication Data

US 2003/0236311 A1 Dec. 25, 2003

Related U.S. Application Data

(60) Provisional application No. 60/381,710, filed on May 20, 2002.

(51) Int. Cl.$^7$ .............................................. C07C 33/08
(52) U.S. Cl. ........................ 568/840; 568/840; 568/876
(58) Field of Search ................................. 568/840, 876

(56) References Cited

U.S. PATENT DOCUMENTS 5,821,111 A * 10/1998 Grady et al. .............. 435/252.5

* cited by examiner

*Primary Examiner*—Johann Richter
*Assistant Examiner*—Lansana Nyalley
(74) *Attorney, Agent, or Firm*—Nancy E. Hill; Hill & Schumacher

(57) ABSTRACT

A process for producing saleable liquids from organic material comprising the following steps. Providing organic material and separating it into solids, liquids and vapor. Reacting the liquids, combining it with water vapor and producing a volatized gas stream. Removing nitrogen dioxide from the gas stream to produce a scrubbed volatized gas stream. Reacting the scrubbed volatized gas stream with water vapor to produce a combined volatized gas stream. Removing carbon dioxide from the combined volatized gas stream to produce a subtracted volatized gas stream. Reacting the subtracted volatized gas stream with methanol to produce an enhanced volatized gas stream. Distilling the enhanced volatized gas stream to produce ethanol.

33 Claims, 2 Drawing Sheets

PROCESS FOR PRODUCING SALEABLE LIQUIDS FROM ORGANIC MATERIAL

CROSS REFERENCE TO RELATED PATENT APPLICATION

This patent application relates to U.S. Provisional Patent Application Ser. No. 60/381,710 filed on May 20, 2002 entitled Process for producing ethanol from sewage sludge which is Incorporated herein by reference.

FIELD OF THE INVENTION

This invention relates to the production of ethanol from the processing of dewatered sewage sludge.

BACKGROUND OF THE INVENTION

Sewage sludge is typically processed by municipalities into a product called "cake". This is the result of incubation with specialized bacteria for a prescribed length of time, then processing with a polymer prior to squeezing as much water out of the mixture as possible. The cake so formed is then disposed of in a variety of ways, all of which have problems. The most common means of disposal has been incineration, but studies are revealing that the metals, some of which are toxic, present in the sewage are accumulating in the soils around incinerators.

The second most prevalent means of disposal is the spreading of the partially processed sewage on agricultural, park, and other land. The sewage still has a significant number of pathogens present, however, which limits the type of crop grown and the time in which the harvest can safely be made. Sewage which is processed more than that used directly on the land is sometimes used for other types of fertilizer. The extent to which this can be done depends on the thoroughness of the processing, and the survival of some of the pathogens.

Some sewage sludge, (the cake), is sometimes landfilled. The persistent bacterial activity causes more methane to form than other waste. The problem of pathogen- and metal-leaching into the groundwater remains a concern.

All in all, the sewage remains a problem which has not resulted in a good solution. Sewage is a good source of organic feedstock for selected processes, and is underutilized.

SUMMARY OF THE INVENTION

According to the invention a process for producing saleable liquids from organic material comprises the following steps. Providing organic material and separating it into solids, liquids and vapour. Reacting the liquids, combining it with water vapour and producing a volatized gas stream. Removing nitrogen dioxide from the gas stream to produce a scrubbed volatized gas stream. Reacting the scrubbed volatized gas stream with water vapour to produce a combined volatized gas stream. Removing carbon dioxide from the combined volatized gas stream to produce a subtracted volatized gas stream. Reacting the subtracted volatized gas stream with methanol to produce an enhanced volatized gas stream. Distilling the enhanced volatized gas stream to produce ethanol.

In another aspect of the invention dewatered sewage sludge is dried continuously in a vessel at temperatures sufficient to volatize the water, leaving behind the organic components of the sludge. The steam produced by drying the sludge is used in another part of the process. The dried solids are then volatized in an oxygen-free vessel. The gas stream emerging is cleaned by conventional methods and scrubbed to remove chlorine and sulfur. The gases are then compressed and reacted in a heated vessel with steam and a catalyst to form a synthesis gas.

A calculated amount of biomass, typically wood waste, is steam-gasified in a separate vessel. The gases evolved are cleaned and compressed. Any carbon removed from the gas stream is processed with the sludge gases in the same reactor to form a synthesis gas. The compressed gases are reacted in a pressurized heated vessel to form methanol. The methanol is then processed in a separate heated vessel with a catalyst, and the synthesis gases from the sludge, to form ethyl alcohol (ethanol).

The vaporous mixture of alcohol and steam is cooled. Any unrecombined gases present are recycled through the burner used to heat the retorts used for drying the sewage or gasifying the biomass. The liquids from the cooler are then distilled to separate the ethanol and the water. Some water is recycled into the system, but there is excess which is removed from the process.

Both the retorts for the biomass gasification and the sludge volatizing are heated indirectly by the partial combustion of methane or a suitable mixture of combustible gases. The spent gases are blended in with the biomass gases to enhance the process yields and decrease air emissions.

Further features of the invention will be described or will become apparent in the course of the following detailed description.

BRIEF DESCRIPTION OF THE DRAWINGS

The invention will now be described by way of example only, with reference to the accompanying drawings, in which.

DETAILED DESCRIPTION OF THE INVENTION

Figure 1:
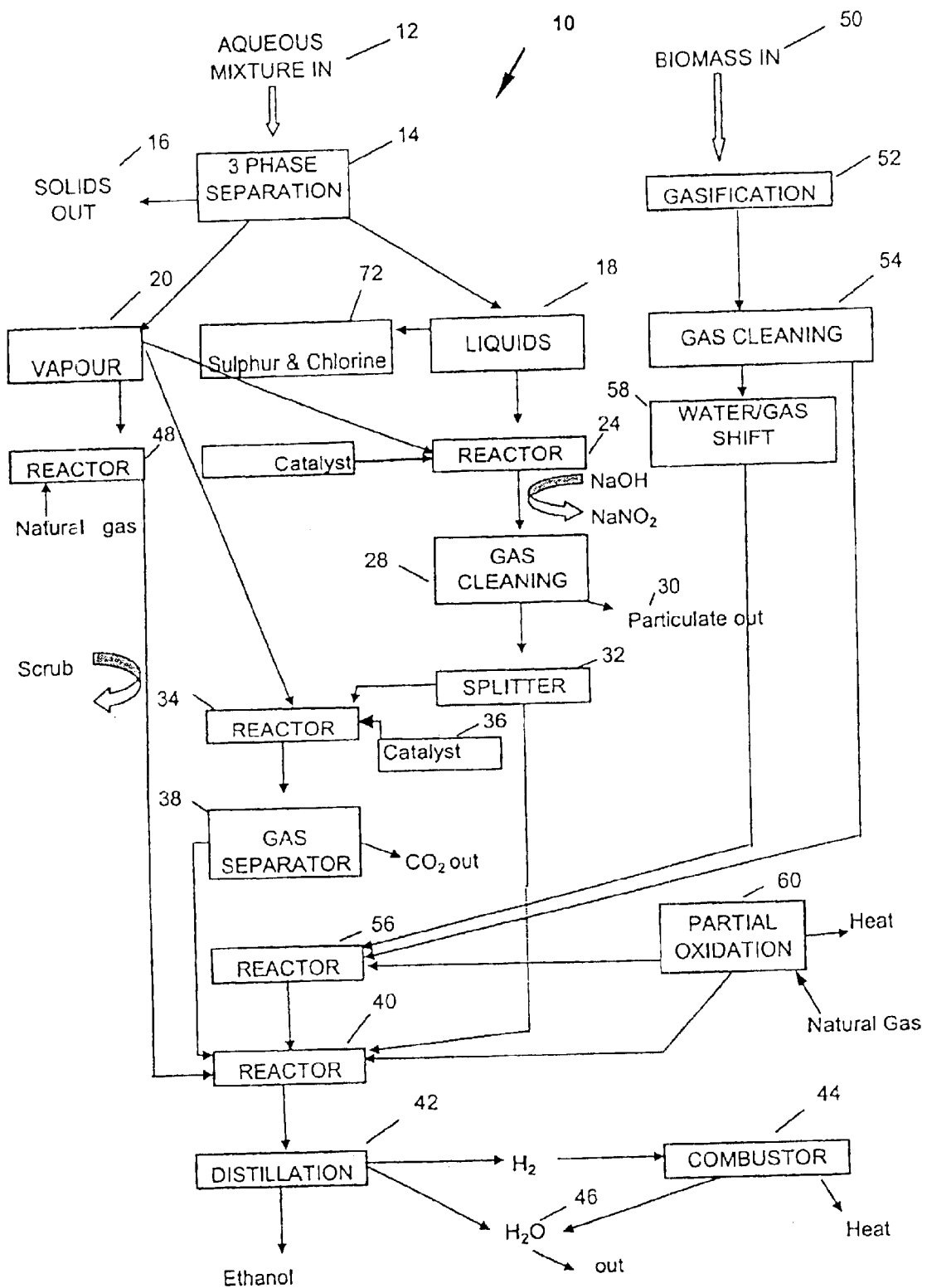
FIG. 1 is a flow chart of a process for converting organic material into saleable liquids.

Referring to FIG. 1 the process is shown generally at 10. A mixture 12 of organic material mixed with water is pumped into a separator 14 wherein generally in the absence of oxygen (air) the mixture is separated into solids 16, liquids 18 and gases or vapour 20. The mixture 12 can be from 5–99% moisture (water). The process is particularly useful for the processing of sewage sludge. The pump is selected according to mixture consistency.

The separator 14 is heated at least to 115° C. However the temperature depends on the percentage of solids in mixture 12. The separator 14 is slightly sub-atmospheric resulting from the gases being withdrawn. The solids 16 are removed from the process. The amount of moisture in the organic material and the temperature selected will determine the dwell time in the separator 14.

Sulfur and chlorine are removed from the liquid as shown at 22. These may be removed by passing the liquid 18 through an iron sponge. The liquids are then passed into a reactor 24 where they are heated to between 225 and 300° C. at 7400–7600 kpa. A catalyst 26 is added to the reactor 24. The catalyst is cobalt (Co) on a ceramic or the like. In addition a portion of the vapour 20 which is generally water vapour is added. In reactor 24 generally a gas stream containing $CO+H_2+NO_2$ is formed.

Gas stream is then cleaned or scrubbed 28 wherein NaOH is sprayed on the gas stream so that the $NO_2$ in the gas stream combines to form $NaNO_2$ which is removed thereafter. The gas also has particulate removed 30. The gas is the remaining gas which is generally CO and $H_2$ is split into two streams in splitter 32.

One portion of the gas stream is processed by a second reactor 34 wherein the gas stream is heated to 225–300° C. at 7400–7600 kpa. A catalyst 36 is introduced which is iron (Fe) and cobalt (Co) on a silica base or the like. As well a portion of the vapour 20 is introduced into reactor 34. The gas is then separated 38 into $CO_2+H_2+H_2O$. The $CO_2$ is removed from the gas stream.

The gas stream is then passed into a third reactor 40 wherein $H_2$ and $H_2O$ are combined with methanol. Third reactor 40 combines gases from four gas streams described in more detail below. Third reactor is at a range of 350–380° C. and a pressure of 19,443 to 21,490 kpa in the presence of catalyst such as iron and cobalt on a silica base. The gas stream is distilled 42 into three components, specifically $H_2$, $H_2O$ and ethanol. The $H_2$ is passed to a combustor 44 wherein it is combusted with oxygen and the combustor is used as a heat source. The water 46 is removed.

The water vapour 20 discussed above is divided into three streams. One stream is added to reactor 24, another stream is added to second reactor 34 and the third stream is passed fourth reactor 48. In the fourth reactor the gas stream is reacted with natural gas at a temperature of 225–300° C.; 7400–7600 kpa in the presence of a catalyst Fe and CO on silica.

If necessary sulfur and chlorine are removed from the liquid with an iron sponge. Similarly the gas may be scrubbed wherein NaOH is sprayed on the gas stream so that the $NO_2$ in the gas stream combines to form $NaNO_2$ which is removed. This gas stream is then passed to third reactor 40.

A separate stream may be used to produce methanol that is added to the gas stream. For example the input may be biomass 50. The biomass is gasified 52 in for example a fluid bed gasifier. The handling of the biomass is determined by the particular gasification method chosen and the moisture content of the particular biomass chosen. It may be that predrying is included. The heat for gasification may be provided by combustor 44. The gasification is provided at 650–900° C., and preferably at 650 C. Gasification generally takes place in the absence of oxygen. The gas stream is cleaned 54 to remove carbon particles. The gas stream is passed to a fifth reactor 56. The carbon particles are processed via a water/gas shift 58 to produce syngas. This takes place at a temperature of 225–300° C. and pressure 7400–7600 kpa in the presence of a catalyst which is a Fe and Co on silica base. The resulting syngas are then passed to fifth reactor. Natural Gas is combusted 60 using sub-stoichiometric oxygen ($O_2$) (ratio 2:1) to produce heat and syngas. The heat is used for gasification or other reactors where heat is required. The syngas is directed to fifth reactor 56.

In reactor 56 the three gas streams are heated to a temperature of 200–300° C. and pressure of 50–150 atm in the presence of a catalyst Copper-zinc oxide-aluminium oxide, or selected from the group of state-of-the-art catalysts.

As discussed above preferably heat for the process is provided by the combustor 44 and partial oxidation of the natural gas 60.

Figure 2:
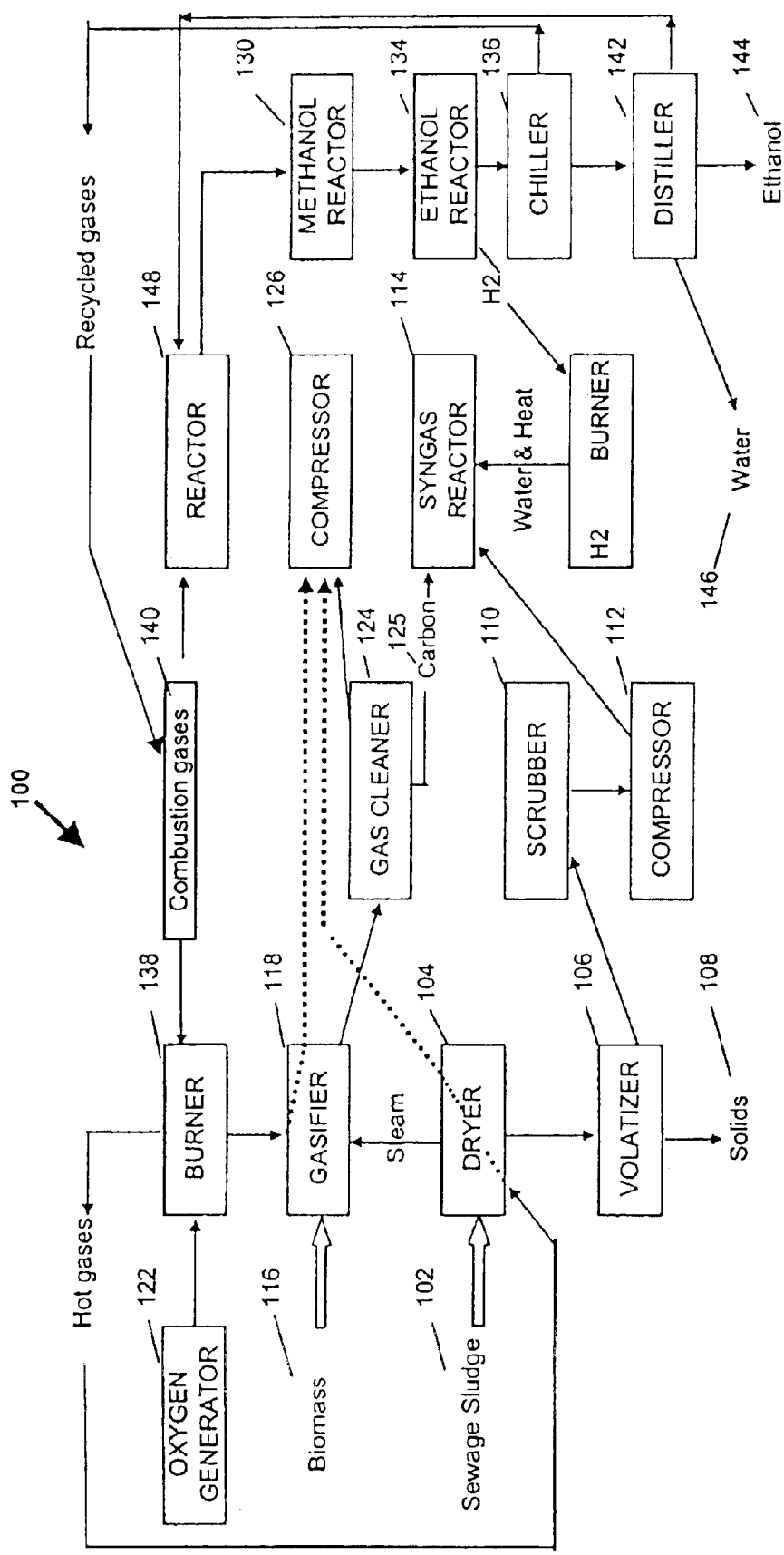
FIG. 2 is a schematic representation of an apparatus in accordance with the present invention for producing ethanol from sewage sludge.

Referring to FIG. 2 an apparatus for producing ethanol for sewage sludge is shown generally at 100. Dewatered sewage sludge 102 containing on average 80% moisture is fed continuously into an air-free drying vessel 104. However it will be appreciated that sludge with a higher water content could also be processed. The temperature is controlled to volatize the water, leaving the organic components without breaking the chemical bonds. Nonvolatized material is continuously removed from the vessel 104 and sent to a gasifier or volatizer 106. Volatizer 106 is also generally air-free, and is heated to a temperature which volatizes the organic compounds without breaking chemical bonds. Inorganic components remain in the vessel and are removed at intervals 108. The volatized gases exit from the gasifier 106 and are scrubbed 110 to remove chlorine and any other elements such as arsenic. The gases are then compressed 112, then fed into a pressurized catalytic reactor 114 where they are converted into a synthesis gas containing a preponderance of carbon monoxide and hydrogen.

While sewage sludge is being dried and processed, dry biomass 116 with about 20% moisture is fed into a gasifier 118. It will be appreciated by those skilled in the art that biomass with a higher moisture content could also be used but then it would be predried. The gasifier 118 is heated indirectly by the combustion of gases in a burner 138 in the presence of sub-stoichiometric oxygen. The oxygen is produced by an oxygen generator 122, which is set to supply enough oxygen to combust the gases to form maximum carbon monoxide and hydrogen. The gasifier is fed with steam exiting from the sewage dryer 104 to steam-gasify the biomass. The gases emerge from the gasifier 118 and are cleaned 124 by the removal of particulate matter 125. The particulate matter 125 which is typically carbon is collected and sent to the synthesis gas reactor 114. The gases from the gas cleaner 124 are first compressed 126 then sent to a heated reactor with a catalyst selected to form methyl alcohol (methanol) 130.

The products from the methanol reactor 130 are sent to a heated pressure vessel or ethanol reactor 134 which has a catalyst selected to form ethyl alcohol (ethanol). The vapor stream emerging from the ethanol reactor 134 is cooled in a chiller 136, and the liquids sent on to a distillation column 142. If there are gases present in the chiller 136, they are sent to the burner at 138 and mixed with the combustion gases 140.

The distillation column 142 separates the ethanol 144 from water 146. The ethanol 144 is removed from the process for sale. Some of the water 146 is used to supply internal processes such as the reactor 148. This reactor 148 supplies additional synthesis gas to the methanol reactor 130 by the processing of methane with water. The water 146 not needed in the system is removed from the process.

Combustion gases are needed for heating at several stages in the process. They are supplied to burner 138 and are burned in the presence of sub-stoichiometric oxygen supplied by the oxygen generator 122. The resulting spent gases are high in carbon monoxide and hydrogen and merge with the stream from the gas cleaner 124 where they are compressed 126 prior to entering the methanol reactor 130. The burner 138 also supplies hot gases to indirectly heat the dryer for the sewage sludge 104. The spent gases are then compressed 126 and sent to the methanol reactor 130.

As used herein, the terms "comprises" and "comprising" are to be construed as being inclusive and opened rather than exclusive. Specifically, when used in this specification including the claims, the terms "comprises" and "comprising" and variations thereof mean that the specified features, steps or components are included. The terms are not to be interpreted to exclude the presence of other features, steps or components.

It will be appreciated that the above description related to the invention by way of example only. Many variations on the invention will be obvious to those skilled in the art and such obvious variations are within the scope of the invention as described herein whether or not expressly described.

What is claimed is:

1. A process for producing saleable liquids from organic material comprising the steps of:
   providing organic material generally in the absence of oxygen and separating it into solids, liquids and vapour;
   reacting the liquids, combining it with water vapour and producing a volatized gas stream;
   removing nitrogen dioxide from the gas stream to produce a scrubbed volatized gas stream;
   reacting the scrubbed volatized gas stream with water vapour to produce a combined volatized gas stream;
   removing carbon dioxide from the combined volatized gas stream to produce a subtracted volatized gas stream;
   reacting the subtracted volatized gas stream with methanol to produce an enhanced volatized gas stream; and
   distilling the enhanced volatized gas stream to produce ethanol.

2. A process for producing saleable liquids from organic material as claimed in claim 1 further including the step of removing sulfur and chlorine from the liquid before volatizing the liquid.

3. A process for producing saleable liquids from organic material as claimed in claim 2 wherein the scrubbed gas is divided into two portions and one portion reacted to produce the combined volatized gas stream and the other portion is reacted to produce the enhanced gas stream.

4. A process for producing saleable liquids from organic material as claimed in claim 3 wherein vapour from the organic material is divided into at least two vapour steams and one water vapour stream is used in the reacting step to produce volatized gas stream and the second water vapour stream is used in the reacting step to produce combined volatized gas stream.

5. A process for producing saleable liquids from organic material as claimed in claim 4 wherein the vapour is split into three streams and the third water vapour stream is reacted to produce a volatized vapour stream which is reacted with the enhanced volatized gas stream.

6. A process for producing saleable liquids from organic material as claimed in claim 5 wherein nitrogen is removed from the volatized vapour stream to produce a scrubbed volatized vapour stream and the scrubbed volatized vapour stream is reacted with the enhanced volatized gas stream.

7. A process for producing saleable liquids from organic material as claimed in claim 6 wherein the methanol is produced from biomass.

8. A process for producing saleable liquids from organic material as claimed in claim 7 wherein the biomass is processed with the steps of:
   gasifying the biomass in the presence of steam and generally in the absence of oxygen to produce a biomass gas stream;
   removing carbon particles from the gas stream to produce a cleaned biomass gas stream and water;
   processing carbon particles via water/gas shift to produce syngas
   combining cleaned biomass gas stream and syngas with the enhanced volatized gas stream.

9. A process for producing saleable liquids from organic material as claimed in claim 8 wherein in the distillation step water and hydrogen are also produced.

10. A process for producing saleable liquids from organic material as claimed in claim 9 wherein the hydrogen is combusted to provide heat to the system.

11. A process for producing saleable liquids from organic material as claimed in claim 10 wherein heat is provided to the process by partially oxidizing natural gas in the presence of sub-stoichiometric oxygen and the gases from this process are reacted with the enhanced volatized gas stream.

12. A process for producing saleable liquids from organic material as claimed in claim 11 wherein the nitrogen dioxide is removed by spraying the volatized gas stream with sodium hydroxide to form sodium nitrite.

13. A process for producing saleable liquids from organic material as claimed in claim 12 wherein the nitrogen dioxide is removed by spraying the volatized vapour gas stream with sodium hydroxide to form sodium nitrite.

14. A process for producing saleable liquids from organic material as claimed in claim 13 wherein the biomass gas stream, the water vapour from the biomass and the gases from the partial oxidizing of natural gas are reacted in a fifth vessel prior to reacting with the volatized gas stream.

15. A process for producing saleable liquids from organic material as claimed in claim 14 wherein the gas from partially oxidizing natural gas is divided into two gas streams one gas stream being added to the fifth vessel and the other gas stream being added to the reacting step to produce the enhanced volatized gas stream.

16. A process for producing saleable liquids from organic material as claimed in claim 15 wherein the volatizing step is in a first vessel which is heated to a temperature of between 225 and 300° C. and at a pressure of between 7400 and 7600 kpa.

17. A process for producing saleable liquids from organic material as claimed in claim 16 wherein a catalyst of cobalt is introduced into the first vessel.

18. A process for producing saleable liquids from organic material as claimed in claim 17 wherein the cobalt is on a ceramic.

19. A process for producing saleable liquids from organic material as claimed in claim 18 wherein the combining of the scrubbed volatized gas stream is in a second vessel which is heated to between 225 and 300° C. and a pressure of between 7400 and 7600 kpa.

20. A process for producing saleable liquids from organic material as claimed in claim 19 wherein a second catalyst of iron and cobalt is introduced into the second vessel.

21. A process for producing saleable liquids from organic material as claimed in claim 20 wherein the iron and cobalt of the second catalyst is on a silica.

22. A process for producing saleable liquids from organic material as claimed in claim 21 wherein the combining of the subtracted volatized gas stream is in a third vessel which is heated to between 350 and 380° C. and a pressure of between 19,443 and 21,490 kpa.

23. A process for producing saleable liquids from organic material as claimed in claim 22 a third catalyst of iron and cobalt is introduced into the third vessel.

24. A process for producing saleable liquids from organic material as claimed in claim 23 wherein the iron and cobalt of the third catalyst are on a silica.

25. A process for producing saleable liquids from organic material as claimed in claim 24 wherein the volatizing of the vapour is in a fourth vessel which is heated to between 225 and 300° C. and a pressure of 7400 to 7600 kpa.

26. A process for producing saleable liquids from organic material as claimed in claim 25 wherein a fourth catalyst of iron and cobalt is introduced into the fourth vessel.

27. A process for producing saleable liquids from organic material as claimed in claim 26 wherein the iron and cobalt of the fourth catalyst are on a silica.

28. A process for producing saleable liquids from organic material as claimed in claim 27 wherein the combining of the subtracted volatized gas stream is in a fifth vessel which is heated to between 225 and 300° C. and a pressure of between 7400 and 7600 kpa.

29. A process for producing saleable liquids from organic material as claimed in claim 20 wherein a fifth catalyst of iron and cobalt is introduced into the fifth vessel.

30. A process for producing saleable liquids from organic material as claimed in claim 21 wherein the iron and cobalt of the fifth catalyst are on a silica.

31. A process for producing saleable liquids from organic material as claimed in claim 30 wherein the gasification of the biomass takes place at a temperature between 650 and 900° C.

32. A process for producing saleable liquids from organic material as claimed in claim 1 wherein the methanol is produced from biomass.

33. A process for producing saleable liquids from organic material as claimed in claim 32 wherein the biomass is processed with the steps of:

gasifying the biomass in the presence of steam and generally in the absence of oxygen to produce a biomass gas stream;

removing carbon particles from the gas stream to produce a cleaned biomass gas stream and water;

processing carbon particles via water/gas shift to produce syngas; and combining cleaned biomass gas stream and syngas with the enhanced volatized gas stream.

* * * * *